United States Patent
Fisher et al.

(10) Patent No.: US 10,034,960 B2
(45) Date of Patent: Jul. 31, 2018

(54) COMPOSITIONS AND METHODS FOR MAKING BIODEGRADABLE STRUCTURES

(71) Applicants: University of Maryland, College Park, College Park, MD (US); Children's National Medical Center, Washington, DC (US)

(72) Inventors: John Patrick Fisher, Kensington, MD (US); Anthony Melchiorri, Ellicott City, MD (US); Narutoshi Hibino, Columbus, OH (US); Axel Krieger, Alexandria, VA (US); John P. Costello, Washington, DC (US); Carolyn Cochenour, Washington, DC (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 14/895,617

(22) PCT Filed: Jun. 6, 2014

(86) PCT No.: PCT/US2014/041296
§ 371 (c)(1),
(2) Date: Dec. 3, 2015

(87) PCT Pub. No.: WO2014/197790
PCT Pub. Date: Dec. 11, 2014

(65) Prior Publication Data
US 2016/0136326 A1 May 19, 2016

Related U.S. Application Data

(60) Provisional application No. 61/831,983, filed on Jun. 6, 2013, provisional application No. 61/917,808, filed on Dec. 18, 2013, provisional application No. 61/832,010, filed on Jun. 6, 2013.

(51) Int. Cl.
| | |
|---|---|
| A61L 27/16 | (2006.01) |
| C08G 63/91 | (2006.01) |
| A61L 27/22 | (2006.01) |
| A61L 27/26 | (2006.01) |
| A61L 27/50 | (2006.01) |
| A61L 27/54 | (2006.01) |
| A61L 27/58 | (2006.01) |
| C08F 267/06 | (2006.01) |
| B33Y 10/00 | (2015.01) |
| B33Y 70/00 | (2015.01) |
| B33Y 80/00 | (2015.01) |

(52) U.S. Cl.
CPC ............ *A61L 27/16* (2013.01); *A61L 27/22* (2013.01); *A61L 27/26* (2013.01); *A61L 27/507* (2013.01); *A61L 27/54* (2013.01); *A61L 27/58* (2013.01); *C08F 267/06* (2013.01); *C08G 63/918* (2013.01); *A61L 2300/252* (2013.01); *A61L 2300/256* (2013.01); *A61L 2300/414* (2013.01); *A61L 2430/20* (2013.01); *B33Y 10/00* (2014.12); *B33Y 70/00* (2014.12); *B33Y 80/00* (2014.12)

(58) Field of Classification Search
CPC .... A61L 27/26; A61L 2300/252; A61L 27/22; A61L 27/227; C08G 63/918; B33Y 70/00
USPC ............ 424/426; 264/401; 514/772; 522/18
See application file for complete search history.

(56) References Cited

U.S. PATENT DOCUMENTS

| 7,589,133 B2 | 9/2009 | Pomrink |
| 2002/0171178 A1 | 11/2002 | Dean |
| 2006/0233855 A1 | 10/2006 | Seliktar |
| 2007/0123977 A1 | 5/2007 | Cottone |
| 2008/0124372 A1 | 5/2008 | Hossainy |
| 2012/0253470 A1 | 10/2012 | Guze |

FOREIGN PATENT DOCUMENTS

JP 2009515659 4/2009

OTHER PUBLICATIONS

Melchels, F., Preparation of Advanced Porous Structures by Stereolithography for Application in Tissue Engineering; PhD Thesis, University of Twente Ensched, Netherlands, Feb. 2010, 199 pages.
Danilevicius, P., et al., Laser-Micro/nanofabricated 3D Polymers for Tissue Engineering Applications, Latvian Journal of Physics and Technical Sciences, 2011, pp. 32-43.

*Primary Examiner* — Yanzhi Zhang
(74) *Attorney, Agent, or Firm* — Hodgson Russ LLP

(57) ABSTRACT

A composition including PPF or a PPF copolymer that can be used to fabricate biodegradable structures. The composition can be used in 3-D patterning (e.g., 3-D printing and sterolighography) methods. For example, 3-D patternable compositions include PPF or a PPF copolymer, a photoinitiator or photoinitiators, and a resolution control inhibitor or inhibitors. The compositions can be used to make biodegradable structures (such as cardivascular scaffolds). The biodegradable structures can be surface functionalized. The biodegradable structures can be used in methods of blood delivery in an individual.

6 Claims, 11 Drawing Sheets

Table 1

| DEF:PPF Ratio | PPF Molecular Weight | BAPO | Inhibitor 1 | Inhibitor 2 | Light Brightness (mW/dm²) | Exposure Time for 50 Micron Layer | Results |
|---|---|---|---|---|---|---|---|
| 1:8 | 1200 Da | 3% dissolved in methylene Chloride | 2% alpha tocopherol | N/A | 300 | 100s | Resin remained liquid, solid structures did not form; Print did not work |
| 1:8 | 1200 Da | 3% dissolved in methylene Chloride | 2% alpha-tocopherol | N/A | 325 | 100s | Resin remained liquid, solid structures did not form; Print did not work |
| 1:8 | 1200 Da | 3% dissolved in methylene Chloride | N/A | N/A | 300 | 100s | Solid structures were formed, but did not accurately represent the computer models input for the print; Print did not work |
| 1:8 | 1200 Da | 3% dissolved in methylene Chloride | 1.3% alpha-tocopherol | N/A | 250 | 100s | Solid structures were formed, but did not accurately represent the computer models input for the print; Print did not work |
| 4:1 | 1064 Da | 3% dissolved in methylene Chloride | N/A | N/A | 300 | 100s | Resin remained liquid, solid structures did not form; Print did not work |
| 2:1 | 1065 Da | 3% dissolved in methylene Chloride | N/A | N/A | 300 | 100s | Resin remained liquid, solid structures did not form; Print did not work |
| 2:1 | 1065 Da | 3% dissolved in methylene Chloride | 0.06% alpha-tocopherol | N/A | 300 | 100s | Large structures formed, but not as distinct as object intended by computer models |

Figure 8

Table 1 (cont.)

| | | | | | | |
|---|---|---|---|---|---|---|
| 46:1 | 1065 Da | 3% dissolved in methylene Chloride | 0.12% alpha-tocopherol | N/A | 275 | 100s | Print roughly successful, though porous features in test shapes were largely non-existent. Overall height of parts intact. |
| 8:1 | 1065 Da | 3% dissolved in methylene Chloride | 0.12% alpha-tocopherol | N/A | 275 | 50s | Print successful; higher resolution achieved with shorter time (50s vs 100s exposure), although 450 micron pores were not fully formed. |
| 8:1 | 1065 Da | 3% dissolved in methylene Chloride | 0.24% alpha-tocopherol | N/A | 275 | 50s | Build unsuccessful. No solid structures attached to buildplate. |
| 8:1 | 1065 Da | 3% dissolved in methylene Chloride | 0.5% alpha-tocopherol | N/A | 275 | 100s | Build unsuccessful. No solid structures attached to buildplate. |
| 8:1 | 1300 Da | 3% dissolved in methylene Chloride | .12% alpha-tocopherol | N/A | 275 | 50s | Somewhat successful. Parts malformed. |
| 8:1 | 1300 Da | 3% dissolved in methylene Chloride | .16% alpha-tocopherol | N/A | 285 | 50s | Parts not able to build plate; print unsuccessful |
| 4:1 | 1300 Da | 3% dissolved directly into DEF | N/A | N/A | 275 | 100s | Parts did not stick to build plate; parts printed completely. |
| 1:1 | 1300 Da | 3% dissolved directly into DEF | .16% | N/A | 275 | 50s | Mostly successful, though not all parts printed completely. |
| 1:1 | 1000 Da | 3% dissolved directly into DEF | N/A | N/A | 275 | 50s | Mostly successful, though not all parts printed completely. Prints turned out well. |

Figure 8 (cont.)

Table 1 (cont.)

| | | | | | |
|---|---|---|---|---|---|
| 1:1 | 1000 Da | 3% dissolved directly into DEF | 0.35% alpha-tocopherol | N/A | 275 | 50s | Prints did not turn out, structures not fully formed |
| 1:1 | 1000 Da | 3% dissolved directly into DEF | 02.5% alpha-tocopherol | N/A | 275 | 50s | Prints turned out well |
| 1:1 | 1000 Da | 3% dissolved directly into DEF | .10% alpha-tocopherol | .10% OrangeG | 275 | 100s | Test grafts formed mostly according to computer model inputs, but OrangeG appeared to fall out of solution. Where OrangeG remained, resolution appeared improved. |
| 1:1 | 1000 Da | 3% dissolved directly into DEF | .10% alpha-tocopherol | 10% TiO | 275 | 50s | Base printed but structures mostly did not |
| 1:1 | 1000 Da | 0.5% dissolved directly into DEF | .10% alpha-tocopherol | .10% TiO | 275 | 100s | Base printed, but structures mostly did not |
| 1:1 | 1000 Da | 1.0% dissolved directly into DEF | 10% HMB | N/A | 275 | 100 | Print did not work |
| 1:1 | 1000 Da | 1.0% dissolved directly into DEF | 10% HMB | N/A | 275 | 100 | Print fared better than with 0.5% BAPO, but did not completely form |
| 1:1 | 1000 Da | 2.0% dissolved directly in DEF | 1% HMB | N/A | 275 | 100 | Print formed mostly but resolution not high and not all parts completed printing. Print did not fully form |

Figure 8 (cont.)

Table 1 (cont.)

| | | | | | | |
|---|---|---|---|---|---|---|
| 1:1 | 1000 Da | 1% dissolved directly into DEF | 10% HMB | 1% TiO₂ | 275 | 150s | Print did not fully form |
| 1:1 | 750 Da | 1% dissolved directly into DEF | 0.1% HMB | N/A | 275 | 100s | Print did not fully formed |
| 8:1 | 750 Da | 1% dissolved directly into DEF | 1% alpha-tocopherol | N/A | 275 | 100s | Print not fully formed |
| 8:1 | 1000 Da | 1% dissolved directly into DEF | .1% TiO₂ | N/A | 275 | 100s | Print did not fully form |
| 8:1 | 1000 Da | 1% dissolved directly into DEF | 1% alpha-tocopherol | N/A | 275 | 100s | Print worked for most parts, but could not print cylindrical grafts with thicknesses of 100 microns or less |
| 8:1 | 1000 Da | 1% dissolved directly into DEF | 2% alpha-tocopherol | N/A | 275 | 100s | Successful print, although resolution still not optimal |
| 8:1 | 1000 Da | 1% dissolved directly into DEF | 2% alpha-tocopherol | 1% OrangeG | 275 | 100s | Successful print, although OrangeG fell out of solution |
| 8:1 | 1000 Da | 1% dissolved directly into DEF | 2% alpha-tocopherol | 1% OrangeG | 275 | 50s | Successful print, although OrangeG fell out of solution |
| 1:1 | 1000 Da | 1% dissolved directly into DEF | 20% HMB | 1% TiO₂ | 280 | 60s | Print unsuccessful (used a formulation akin to that of Cox-Western Formula) |
| 8:1 | 1000 Da | 1% dissolved directly into DEF | 1% alpha-tocopherol | 1% HMB | 275 | 50s | Successful print, good resolution |
| 8:1 | 1000 Da | 1% dissolved directly into DEF | 2% alpha-tocopherol | 5% HMB | 275 | 50s | Print successful for parts |

Figure 8 (cont.)

Table 1 (cont.)

| | | | | | |
|---|---|---|---|---|---|
| 8:1 | 780 Da | 1% dissolved directly into DEF | 2% alpha-tocopherol | 4% HMB | 275 | 5.0s | with dimensions larger than 150 microns, but did not work for smaller grafts with features less than 100 microns. Print successful |
| 8:1 | 795 Da | 1% dissolved directly into DEF | 2% alpha-tocopherol | 1% HMB | 265 | 5.0s | Prints successful |
| 8:1 | 795 Da | 1% dissolved directly into DEF | 2% alpha-tocopherol | 4% HMB | 275 | 5.0s | Prints successful and sent to be implanted in Mice |
| 8:1 | 795 Da | 1% dissolved directly into DEF | 1% alpha-tocopherol | 1% HMB | 275 | 5.0s | Prints successful |
| 8:1 | 830 Da | 1% dissolved directly into DEF | 1% alpha-tocopherol | 4% HMB | 275 | 5.0s | Prints successful |
| 8:1 | 880 Da | 1% dissolved directly into DEF | 2% alpha-tocopherol | 1% HMB | 275 | 5.0s | prints successful |
| 8:1 | 710 Da | 1% dissolved directly into DEF | 2% alpha-tocopherol | 4% HMB | 275 | 5.0s | Prints successful |
| 8:1 | 1500 Da | 1% dissolved directly into DEF | 1% alpha-tocopherol | 1% HMB | 275 | 5.0s | Prints successful |

Figure 8 (cont.)

Table 2

| Vessel | Average Length (mm) | Average Diameter (µm) |
|---|---|---|
| Artery | 17.0 | 52.6 |
| Small arter | 3.5 | 19.0 |
| Arteriole | 0.95 | 7.0 |
| Capillary | 0.23 | 3.7 |
| Post-capillary venule | 0.21 | 7.3 |
| Venule | 1.0 | 21.0 |
| Small vein | 3.4 | 37.0 |
| Vein | 16.6 | 76.2 |

COMPOSITIONS AND METHODS FOR MAKING BIODEGRADABLE STRUCTURES

CROSS REFERENCE TO RELATED APPLICATIONS

This application claims priority to U.S. Provisional Patent Application No. 61/831,983, filed on Jun. 6, 2013, U.S. Provisional Patent Application No. 61/832,010, filed on Jun. 6, 2013, and U.S. Provisional application No. 61/917,808, filed on Dec. 18, 2013, the disclosures of which are incorporate herein by reference.

STATEMENT REGARDING FEDERAL FUNDING

This invention was made with government support under R01AR061460 awarded by the National Institutes of Science and DGE1322106 awarded by the National Science Foundation. The government has certain rights in the invention.

FIELD OF THE DISCLOSURE

This disclosure generally relates to biodegradable structures and methods of making and using such structures. More particularly, this disclosure relates to biodegradable structures made from a resin based on poly(propylene fumarate) or copolymer thereof and methods of making and using such structures.

BACKGROUND OF THE DISCLOSURE

Heart disease remains the leading cause of death in the United States, affecting nearly 800 million people. Annually, coronary bypass surgeries are required in approximately 250,000 patients, over 50,000 patients are diagnosed with end-stage renal disease, and another 8 million are diagnosed with peripheral arterial disease.

Congenital heart disease is the most common birth abnormality in humans and affects almost 1% of all live births. Approximately 25% of these patients have critical congenital heart disease and require surgical or percutaneous cardiac intervention within the first year of life for survival. Congenital heart disease manifests as a wide variety of structural malformations; due to the diversity of abnormalities, there are various options for palliation and correction.

Vascular grafts are integral to treating aneurysms, vascular reconstruction, congenital cardiovascular disease, and organ transplantation. While autografts may be used as a gold standard, vessel availability may be limited by existing disease conditions or prior surgeries. Investigation of potential synthetic grafts have largely supported the application of poly(ethylene terephthalate) (PET) and expanded poly(tetrafluoroethylene) (ePTFE) grafts in large-diameter (>6 mm) applications. However, grafts for small diameter (<6 mm) applications continue to be challenging because of graft failure due to stenosis.

Tissue engineering approaches offer a potential solution to these challenges. Thus, biodegradable vascular grafts have been constructed from biological and synthetic materials. Small-diameter vascular grafts, however, have experienced a myriad of complications ranging from thrombus formation, aneurysms, intimal hyperplasia, calcium deposition, and noncompliance leading to low patency rates and graft failure.

SUMMARY OF THE DISCLOSURE

We developed a resin based on an aliphatic polyester, poly(propylene fumarate) (PPF). The resin is biodegradable and exhibits tunable viscosity and mechanical properties. The resin can, for example, be used for 3-D (three dimensional) printing to generate biodegradable structures including biodegradable tubular structures such as artificial blood vessels or cardiovascular scaffolds.

In an aspect, this disclosure provides a resin composition comprising PPF, a fumarate, and one or more polymerization initiators. In an embodiment, the resin composition is a 3-D printable resin composition comprising PPF, a fumarate, one or more photoinitiators and one or more photoinhibitors. In an embodiment, the fumarate is diethyl fumarate. In one embodiment, the photoinitiator is BAPO (phenylbis(2,4,6-trimethylbenzoyl)phosphine oxide). In one embodiment, the resin composition comprises PPF, diethyl fumarate, BAPO, α-tocopherol, and hydroxyl-methoxybenzophenone.

In an aspect, this disclosure provides a method for making a biodegradable structure. The biodegradable structure may be an implantable biodegradable structure. In an embodiment, a method such as solvent/mold casting, extrusion, injection molding, electrospinning, in situ crosslinking, 3-D patterning methods (e.g., 3-D printing, sterolithography, digital light processing), or other additive manufacturing methods and a disclosed resin comprising PPF are used to make a biodegradable structure.

In an embodiment, a method for making a biodegradable structure (e.g., a biological tubular structure such as, for example, an artificial blood vessel) comprises providing a 3-D patternable composition comprising PPF, diethyl fumarate, BAPOα-tocopherol, and hydroxyl-methoxybenzophenone, exposing the resin composition to ultraviolet radiation in a manner such that the biodegradable structure is formed.

In an aspect, this disclosure provides a method of providing blood supply to an area within an individual comprising implanting an artificial blood vessel leading up to that area and allowing passage of blood through the blood vessel such that blood supply to the area is provided.

BRIEF DESCRIPTION OF THE FIGURES

FIG. 8. Table 1. Examples of resin composition that resulted in varying levels of success or failure using 3-D printing.

DETAILED DESCRIPTION OF THE DISCLOSURE

The present disclosure provides PPF-based material resins that exhibit, in certain embodiments, desirable resolution control, desirable mechanical properties, and compatibility with 3-D printing fabrication methods. Such a material can be utilized in a variety of applications, especially those necessitating biodegradability or cell-compatibility. The PPF-material resins can be used to fabricate biodegradable structures. The biodegradable structure may be designed as a replacement (or surrogate for) an anatomical structure or structure(s) in an individual (e.g., a human or non-human animal). For example, the biodegradable structure is a graft (e.g., a vascular graft). In another example, the biodegradable structure is a scaffold for the anatomical structure. Also provided are biodegradable structures and uses of the biodegradable structures.

Adjusting the inclusion and concentration of components of the present PPF-based material can tune the resin to be used for a variety of different applications, not limited to, but including tissue engineering. The main component of the resin is PPF (PPF homopolymer or PPF copolymer), which serves as the bulk polymer for fabrication. For example, diethylfumarate (DEF) serves in the synthesis and may also serve as a diluent in the PPF material resin. As a diluent, DEF reduces the viscosity of the resin and enables more efficient and effective printing by providing better material resin flow (e.g., within 3-D printer hardware such as material vats and/or deposition lines). BAPO is an example of a photoinitiator, reacting to light stimulation and initializing the crosslinking between polymer chains during, for example, printing. α-tocopherol (Vitamin E) is an example of an inhibitor that prevents early and excessive crosslinking of PPF polymer chains in an effort to improve printing resolution. Hydroxy-methoxybenzophenone (HMB) is an example of an inhibitor that serves as an ultraviolet light absorber, providing sequestration of the light to enhance printing resolution by preventing unintended crosslinking.

Figures 10, 11:
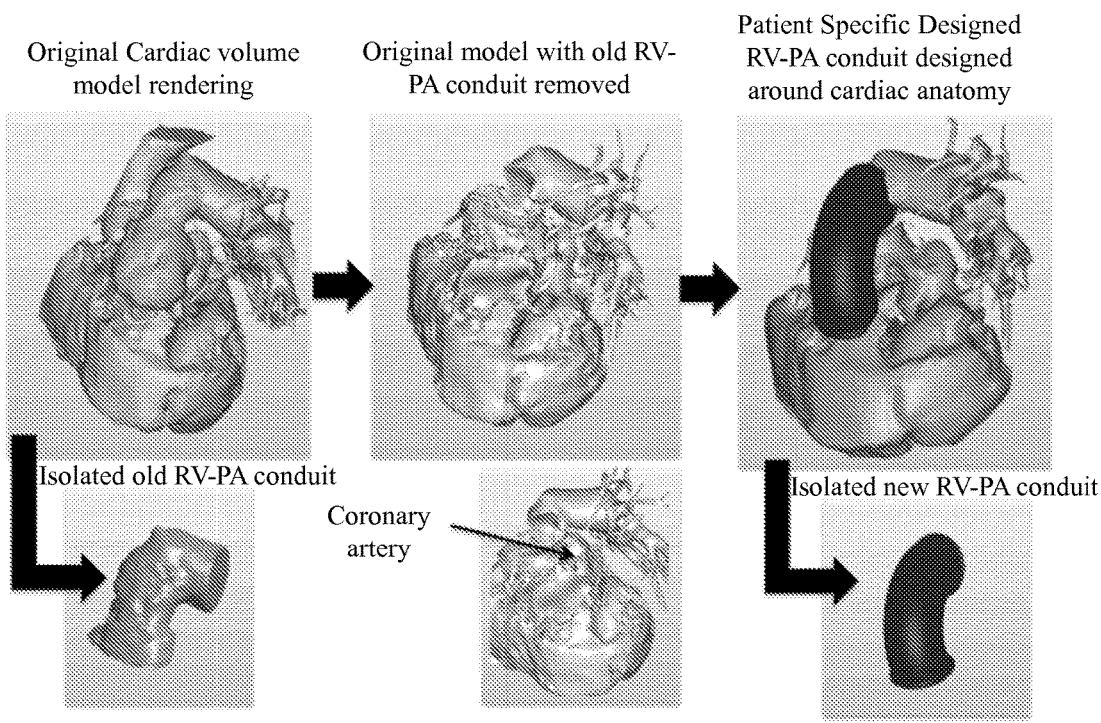
FIG. 10. Table 2. Examples of dimensions of human blood vessels.
FIG. 11. Example of RV-PA construction. Old RV-PA conduit is removed and replaced with a custom RV-PA conduit designed based upon patient's anatomy.

Adjusting the concentration of these components within the resin enables tuning of the mechanical strength and printing resolution (FIG. 10 shows examples of dimensions of human blood vessels). For example, the material resin can be formulated such that devices printed have mechanical properties similar to cardiovascular tissues with relative low elastic moduli (10-15 MPa). Alternatively, formulations can be designed such that 3-D patterned devices have mechanical properties more similar to bone tissue (15-20 GPA). Generally, increasing PPF molecular weight and/or increasing crosslinking increases elastic modulus and decreases compliance. Besides adjusted properties enabling PPF resin suitability for a variety of tissue engineering and medical applications, these properties may be broadly applicable to other fields and purposes.

This disclosure provides, in an embodiment, components specifically designed for 3-D printing, stereolithography, and/or digital light processing techniques of fabrication. In addition, using the material resin the mechanical properties in the fabricated structure can be tuned. For example, mechanical properties of the PPF resin formulation described can be customized to enable printing structures with mechanical properties similar to hard bone or more similar to cardiovascular tissues. This allows the resin to be utilized in a variety of applications where parameters like mechanical strength are crucial to 3-D patterned structure performance.

A graft constructed of PPF has a number of advantages that provide clinical benefit. The material may be tuned for a specific molecular weight to control mechanical properties. Additionally, the method of fabrication may be altered to provide additional control of mechanical properties, e.g., to match native blood vessels. The material is both biodegradable and biocompatible. For example, fumaric acid, a degradation product of PPF, is a natural component of the Kreb's cycle and can be metabolized by cells. This enables, for example, a PPF vascular graft to support the growth of native vessel tissue, while the polymeric components degrade away, leaving behind a healthy blood vessel consisting of the patient's own cells and tissue structures. PPF grafts may also be chemically or structurally modified to enhance cell attachment, proliferation, and differentiation. This can be controlled via surface modification techniques such as, but not limited to, covalent biomolecular crosslinking or 3-D patterning to control surface topography. The various manufacturing methods available to PPF grafts impart these advantages. PPF polymers may be crosslinked, for example via UV irradiation, enabling precise control over polymer chain crosslinking, allowing for precise fabrication of graft architecture and degree of crosslinking, affecting both mechanical properties and cellular/tissue responses.

In an aspect, the present disclosure provides resin compositions comprising PPF. The resin compositions comprise PPF or a copolymer comprising one or more PPF block. The compositions optionally comprise one or more polymerization initiator. The compositions optionally comprise one or more cross-linking monomer/co-monomer. The compositions optionally comprise one or more resolution control inhibitor. The resins can be used to fabricate, for example, biodegradable structures ranging from all manners of bone structures, blood vessels, valve leaflets, ventricles, atriums, septums, or any other cardiac or vascular structure.

In an embodiment, the resin composition is a 3-D patternable composition. The composition is a resin comprising PPF or a copolymer comprising a PPF block. The composition optionally comprises one or more photoinitiator. The composition optionally comprises one or more resolution control inhibitors. The composition optionally further comprises one or more cross-linking monomer/co-monomer. In an embodiment, the composition comprises PPF or a copolymer comprising a PPF block. In an embodiment, the composition comprises PPF or a copolymer comprising a PPF block and a photoinitiator. In an embodiment, the composition comprises PPF or a copolymer comprising a PPF block, a photoinitiator, and resolution control inhibitors. In an embodiment, the composition comprises PPF or a copolymer comprising a PPF block, a photoinitiator, resolution control inhibitors, and a cross-linking monomer/co-monomer.

In an embodiment, the 3-D patternable composition comprises: PPF or copolymer comprising poly(propylene fumarate); a cross-linking monomer/co-monomer selected from alkyl fumarates (e.g., diethyl fumarate); a photoinitiator (e.g., BAPO), and other phosphine oxides, including monoacylphosphine oxides, and trisacylphosphine oxides; α-tocopherol; and hydroxyl-methoxybenzophenone. In an embodiment, components that can adjusted and incorporated within the material resin include: poly(propylene fumarate); diethyl fumarate; BAPO; α-tocopherol (Vitamin E); and hydroxy-methoxybenzophenone (HMB).

PPF is a biodegradable, linear polyester. The polymer is made of fumarate monomer subunits. The polymer degrades into fumaric acid and propylene glycol, which can be cleared from the human body. Variations of PPF may include blends and copolymers with other materials. Examples may include, but are not limited to, poly(propylene fumarate-co-ethylene glycol), poly(propylene fumarate)/poly(lactic-co-glycolic acid), poly(propylene fumarate)-diacrylate, poly(propylene fumarate-co-caprolactone diol), and poly(propylene fumarate)/beta-tricalcium phosphate.

PPF/PPF copolymer can be reacted (e.g., thermally or photochemically crosslinked) such that a 3-D structure is formed. PPF can have a number average molecular weight ($M_n$) of at least 500 g/mol. In an embodiment, PPF has a $M_n$ of at least 700 g/mol. In an embodiment, PPF has a $M_n$ of 500 to 2000 g/mol, including all integer g/mol values and ranges therebetween. In an embodiment, PPF has a $M_n$ of 700 to 1550 g/mol, including all integer g/mol values and ranges therebetween. The PPF copolymer comprises a PPF block. The PPF block can have a molecular weight of 500 to 2000 g/mol, including all integer g/mol values and ranges therebetween. The copolymer has one or more other blocks. For example, these blocks are polyethylene glycol, poly(lactic-co-glycolic acid), poly(caprolactone diol). The PPF or PPF copolymer is present in the composition at 50 to 100% by weight, including all integer % by weight values and ranges therebetween. Suitable PPF or PPF copolymer are commercially available or can be synthesized using methods known in the art.

The PPF may be blended with another polymer or polymers. For example, beta-tricalcium phosphate, poly(lactic-co-glycolic acid), or any other ester-based polymer such as poly(caprolactone fumarate), poly(caprolactone), poly(lactic acid), poly(glycolic acid), or combinations thereof can be blended.

The cross-linking monomer/co-monomer can react to crosslink the PPF or PPF copolymer. Examples of suitable cross-linking monomers/co-monomers include alkyl fumarates (e.g., diethylfumarate, methyl ethylfumarate, diisopropyl fumarate, and dibutyl fumarate). The alkyl groups of the alkyl fumarates have, independently, 1 to 12 carbons, including all integer number of carbons and ranges therebetween. The alkyl groups may have different numbers of carbons. The alkyl groups can be linear or branched. The cross-linking monomer/co-monomer is present in the composition at 0.01 to 50% by weight, including all integer % by weight values and ranges therebetween. In an embodiment, the cross-linking monomer/co-monomer is present in the composition at 20 to 50% by weight. Suitable cross-linking monomer/co-monomer are commercially available or can be synthesized using methods known in the art.

Without intending to be bound by any particular theory, it is considered that use of the cross-linking monomer/co-monomer (e.g., DEF) results in decreased viscosity of PPF resin during fabrication. With regard to fabrication by 3-D patterning (e.g., 3-D printing, stereolithography, and digital light processing), this can enable and ease printing of the resin at room temperature. This eliminates the necessity of heating the printing resin tray and the inclusion of the cross-linking monomer/co-monomer (e.g., DEF) also affects mechanical properties of the resulting fabricated part.

The composition may comprise one or more diluents. For example, the cross-linking monomer/co-monomer can be used as a diluent. It is desirable that the viscosity of the composition, in particular for use in 3-D printing methods, is less than $1 \times 10^4$ cP. In an embodiment, the viscosity of the composition in a 3-D printing method is $1 \times 10^3$ cP to $1 \times 10^4$ cP, including all values to the $10^4$ cP and ranges therebetween.

The composition may comprise one or more organic solvents. Examples of suitable solvents include methylene chloride and acetone. In an embodiment, the composition does not comprise an organic solvent.

The polymerization initiator is a thermal polymerization initiator or photoinitiator. Examples of suitable thermal initiators (free radical initiators) include benzoyl peroxide, N-vinyl pyrrolidone, poly(ethylene glycol)-dimethacrylate, and PPF-diacrylate. Combinations of thermal initiators can be used. Examples of suitable photoinitiators include phosphine oxides such as monoacylphosphine oxides and trisacylphosphine oxides. Combinations of photoinitiators can be used. For example, the photoinitiator is BAPO. The photoinitiator is present in the composition at 0.5 to 3% by weight, including all 0.1% by weight values and ranges therebetween. In an embodiment, the photoinitiator is BAPO (1% w/w) that is dissolved directly into the DEF.

Suitable photoinitiators are known in the art. Examples of suitable photoinitiators include phosphine oxides such as monoacylphosphine oxides and trisacylphosphine oxides. For example, the photoinitiator is BAPO. Combinations of photoinitiators may be used. The photoinitiator is present in the composition at 0.5 to 3% by weight, including all 0.1% by weight values and ranges therebetween. In an embodiment, the photoinitiator is BAPO (1% w/w) that is dissolved directly into the DEF.

Without intending to be bound by any particular theory, it is considered that the resolution control inhibitors provide desirable resolution control in the 3-D printing process. Compositions comprising the resolution control inhibitors can provide 3-D printing of structures at a resolution of less than 50 μm. In an embodiment, the compositions provide 3-D printing of structures at a resolution of 25 μm to 49 μm. Examples of resolution control inhibitors include α-tocopherol, hydroxyl-methoxybenzophenone (HMB), CGL097 (Ciba Ag), hydroquinone, titanium (IV) dioxide, and phenol red. Combinations of resolution control inhibitors can be used. For example, the resolution control inhibitors are α-tocopherol and hydroxyl-methoxybenzophenone, where the α-tocopherol is present at 0.01 to 3% by weight, including all 0.01% by weight values and ranges therebetween, and hydroxyl-methoxybenzophenone is present at t 0.01 to 30% by weight, including all 0.01% by weight values and ranges therebetween.

In an embodiment, the resolution control inhibitor is α-tocopherol at 0.1% to 0.3% w/w or HMB at 1% to 10% w/w. In another embodiment, the resolution control inhibitor is a combination of α-tocopherol at 0.1% to 0.3% w/w and HMB at 1% and 10% w/w.

The composition can be prepared in a variety of manners. For example, the composition is prepared by obtaining a desired mass of PPF or PPF copolymer. The PPF or PPF copolymer is then heated in an oven (e.g., between 60-80° C.) to reduce the viscosity of the polymer. A desired mass of cross-linking monomer/co-monomer (e.g., DEF) is then obtained. A desired mass of each polymerization initiator (and photoinhibitor if present) is obtained separately and then combined into one beaker. After these components are added together, the cross-linking monomer/co-monomer is added to that beaker. The inhibitor (if present)/initiator/ cross-linking monomer/co-monomer mixture is then mixed (e.g., via a stir rod or magnetic stir bar on a stir plate) for approximately 30-60 minutes, or until the inhibitors (if present)/initiators have completely dissolved within the cross-linking monomer/co-monomer. Following this step, the heated PPF or PPF copolymer (at, e.g., 60-80° C.) is added to the beaker containing the inhibitor (if present)/ initiator/ cross-linking monomer/co-monomer mixture. The entire resin mixture is then heated (e.g., at 60-80° C. for 30-60 minutes), or until the PPF or PPF copolymer has completely dissolved into the inhibitor (if present)/initiator/ cross-linking monomer/co-monomer formulation. After dissolution is complete, the mixture is allowed to cool to room temperature under gentle mixing. Once at room temperature, the PPF resin is ready to be used (e.g., in the 3-D printing, stereolithographic, or digit light processing fabrication process).

In another aspect, the present disclosure provides methods for making biodegradable structures. Examples of biodegradable structures include, but are not limited to, all manners of bone structures, blood vessels, valve leaflets, ventricles, atriums, septums, or any other cardiac or vascular structure (such as cardiac valves (aortic, mitral, tricuspid, pulmonary), cardiac valve rings (aortic, mitral, tricuspid, pulmonary), cardiac patches (angioplasty, intraventricular repair, ventricle), cardiac patches with valves, occluders or coils for shunts). In an embodiment, the biodegradable structure is a tubular structure such as a blood vessel. The biodegradable structures may be used as scaffolds. The scaffolds provide a substrate (e.g., a template) on which natural tissues can form and when the biodegradable structure biodegrades the natural tissues form a structure corresponding to the biodegradable structure. In an embodiment, the biodegradable structure is a scaffold (e.g., a cardiovascular scaffold). The instant methods use a 3-D patternable compositions of the instant disclosure. The biodegradable structure may be grafts which are conduits, grafts with valves, grafts with various topography, grafts specific to patient anatomy, or grafts that grow with the patient.

Construction and application of PPF grafts can encompass fabrication techniques including, but not limited to, solvent/ mold casting, 3-D printing, stereolithography (e.g., digital sterolithography), extrusion, injection molding, electrospinning, and in situ crosslinking. Polymer networks of PPF can be crosslinked via thermal and photocrosslinking methods.

Various methods of 3-D patterning can be used. 3-D printing methods may be categorized into groups, such as granular, extrusion, and light polymerized printing. Granular printing may include selective heat or laser sintering, powder bed and inkjet 3-D printing. Sintering techniques utilize selective fusing of materials. Inkjet 3-D printing systems print a layer at a time, functioning similarly to desktop inkjet printers commonly used at home or in the office. Extrusion type printing utilizes fused deposition modeling technology, operating by feeding a material filament through a heated nozzle. Photopolymerization may include stereolithography and digital light processing techniques. Stereolithography is an additive manufacturing process that exposes a photopolymer resin to ultraviolet laser light to cure select portions of the resin, one layer at a time. Digital light processing is similar, but utilizes a projector to cure an entire layer at once based on a projected light mask. This enables curing of an entire layer at once, rather than the voxel-by-voxel approach characteristic of stereolithographic approaches.

PPF vascular grafts may also be fabricated via solvent cast methods in molds. Such a graft may be cured via techniques such as ultraviolet irradiation. Molds may be custom fabricated to produce a PPF vascular graft with a desired shape, size, and features. PPF grafts and PPF copolymer grafts may also be electrospun to produce the desired vascular graft.

During fabrication of a PPF graft, several different polymers and/or chemicals may be utilized to control aspects of fabrication. For example, diethyl fumarate can be added to the PPF to reduce the viscosity of the material before curing. Other diluents may include solvents such as methylene chloride or acetone. Free radical initiators, such as, but not limited to, benzoyl peroxide, N-vinyl pyrrolidone, poly (ethylene glycol)-dimethacrylate, or PPF-diacrylate. Photoinitiators, such as, but not limited to, phenylbis(2,4,6-trimethylbenzoyl)phosphine oxide, can be used to fabricate PPF grafts utilizing ultraviolet light curing.

Figure 1:
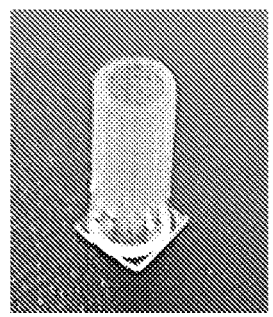
FIG. 1. Vascular graft produced via 3-D printing of a biodegradable, biocompatible material. Base/Support structure for DLP 3-D printing method visible on bottom of graft.
Figure 2:
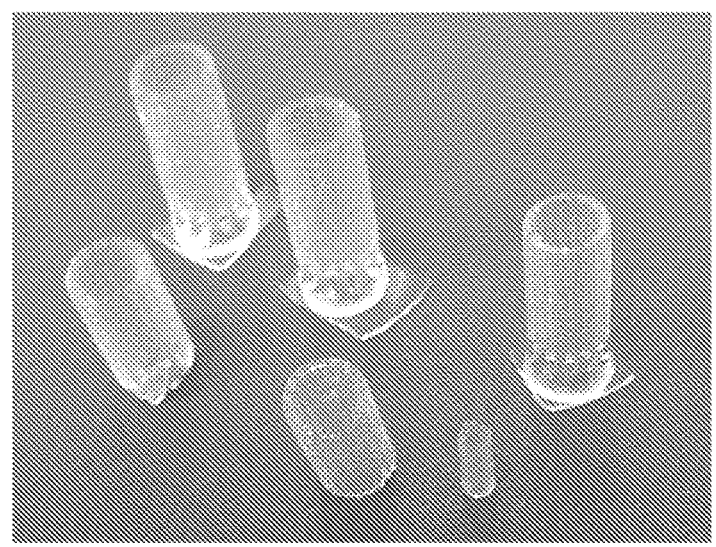
FIG. 2. Examples of various vascular grafts of varying sizes produced via 3-D printing of a biodegradable, biocompatible material. Base/Support structure for DLP 3-D printing method visible on three, rear grafts.

In an embodiment, a method for making a biodegradable structure comprises the steps of: providing a 3-D patternable composition of the instant disclosure; and contacting a selected portion of the composition with visible radiation, ultraviolet radiation, or a combination thereof such that the biodegradable structure is formed. For example, FIGS. 1 and 2 shows examples of a vascular graft made using the method.

By contacting it is meant that the 3-D patternable composition is exposed to or illuminated with visible and/or ultraviolet radiation of wavelengths that result in formation of crosslinking bonds. Sources of visible and/or ultraviolet radiation are known in the art. For example, when BAPO is used the composition is exposed to or illuminated with UV broad spectrum light (e.g., 195 nm to 405 nm). The contacting can be carried out, for example, by 3-D printing, stereolithography, or digital light processing. The contacting can be carried out by sequentially forming discrete layers of the biodegradable structure.

The biodegradable structure may be surface functionalized. A variety of surface modifications be made to PPF structures to enhance in vivo functionality. Surface architecture can be controlled to create features, such as surface roughness and porosity, to enhance cellular attachment, infiltration, and proliferation. Surface architecture may be controlled via fabrication (mold casting or stereolithography) or modified after bulk scaffold fabrication. Examples of post-fabrication physical surface alterations may include porogen leaching, chemical vapor deposition, plasma etching, and UV irradiation. Inclusion of salts during fabrication and curing, such as sodium chloride, and subsequent salt leaching may be used to incorporate random pore architecture.

Figure 9A:
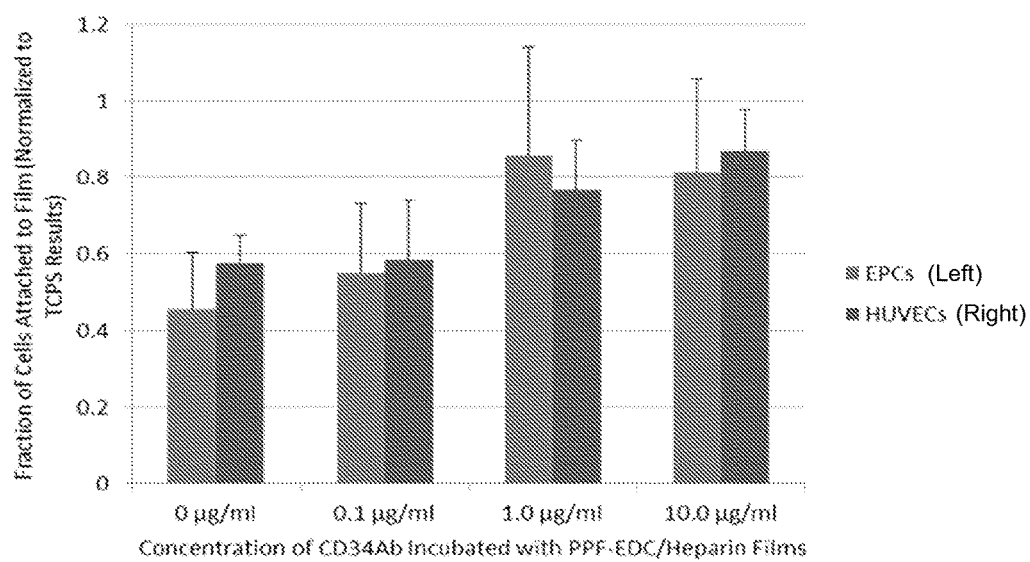
FIG. 9. a) Graph demonstrating attachment of human umbilical vein endothelial cells (HUVECS) and endothelial progenitor cells (EPCs) on 3-D printed biodegradable scaffolds modified with anti-CD34 antibodies via heparin crosslinked to biodegradable material surfaces. Results are normalized to the attachment of cells to normal tissue-culture polystyrene (TCPS). b) Graph demonstrating attachment of human umbilical vein endothelial cells (HUVECS) and endothelial progenitor cells (EPCs) on 3-D printed biodegradable scaffolds modified with vascular endothelial growth factor (VEGF) via heparin crosslinked to biodegradable material surfaces. Results are normalized to the attachment of cells to normal tissue-culture polystyrene (TCPS).
Figure 9B:
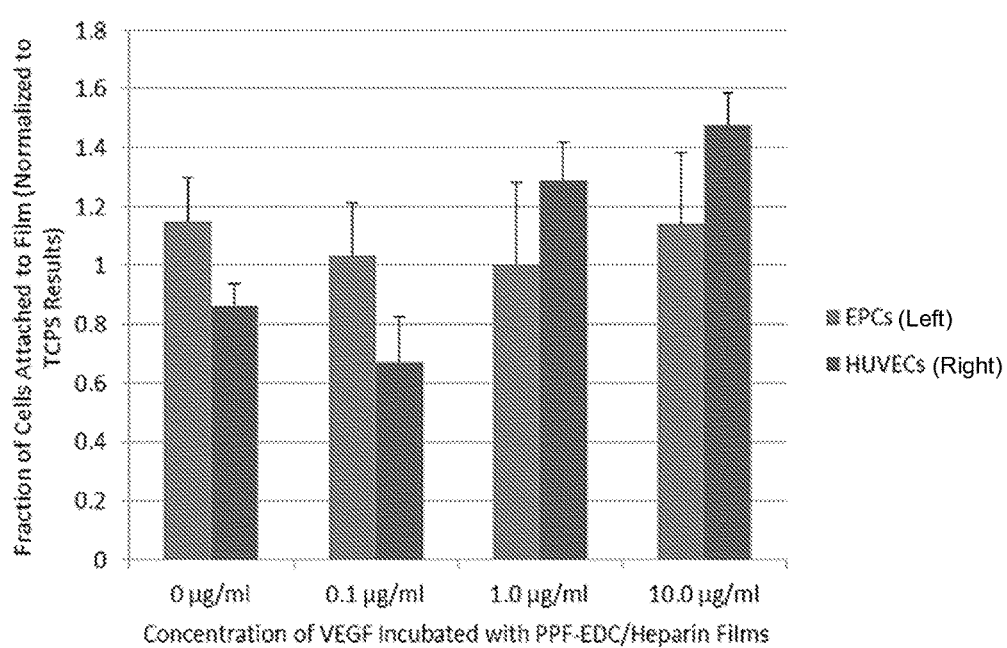

Chemical surface modification may also be utilized to enhance PPF-based scaffold surfaces based on the chemical structure of the polymer Immobilization of biomolecules such as peptide sequences and growth factors may be used. Biofunctional molecules may be included utilizing techniques including, but not limited to, passive coating, covalently linking, and peptide linking. For example, FIGS. 9a and 9b demonstrate functionalization of a biodegradable structure. Surface modifications may be utilized to elicit responses from cells and tissues, such as cell adhesion, proliferation, differentiation, paracrine and endocrine signaling, and morphological adaptation.

In an embodiment, the method further comprises the step of surface functionalizing the biodegradable structure (e.g., artificial blood vessel) such that a biofunctional molecule (e.g., a peptide, a protein, a growth factor, a small signaling molecule, a vitamin, drug, a combination thereof, or a moiety comprising one or more thereof) is non-covalently or covalently attached to a surface of the biodegradable structure. The biological molecule(s) can be covalently bound to the surface of the biodegradable structure by known methods. For example, biological molecule(s) is/are covalently bound to the surface of (i.e., conjugated to) the biodegradable structure using carbodiimide-crosslinker chemistry. The biological molecule(s) can be non-covalently bound to the surface of the biodegradable structure via a linking peptide or linking protein moiety. For example, linking protein(s) or linking peptide(s) is/are covalently bound to the surface of the biodegradable structure (e.g., by carbodiimide-crosslinker chemistry) and the linking protein(s) or linking peptide(s) contacted with biofunctional molecule(s) such that the biofunctional molecule(s) are non-covalently bound to the covalently bound linking protein(s) or linking peptide(s). Such non-covalently bound peptides, proteins, growth factors, small signaling molecules, vitamins, and/or drugs can be released from the surface of the biodegradable structure. In an embodiment, the protein or peptide is an antibody covalently bound to the surface of the biodegradable structure. In an embodiment, the small molecule is a glycosaminoglycan. In an embodiment, the glycosaminoglycan is heparin. In an embodiment, the biodegradable structure is non-covalently surface functionalized with VEGF via a heparin linking protein that is covalently bound to the surface of the biodegradable structure.

Figure 3:
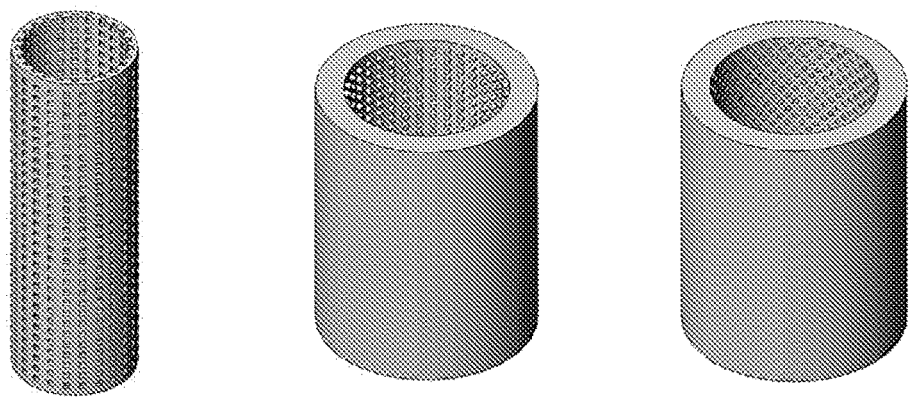
FIG. 3. Various computer-aided designs of grafts that may be fabricated via PPF, utilizing controlled surface architectures.
Figure 4:
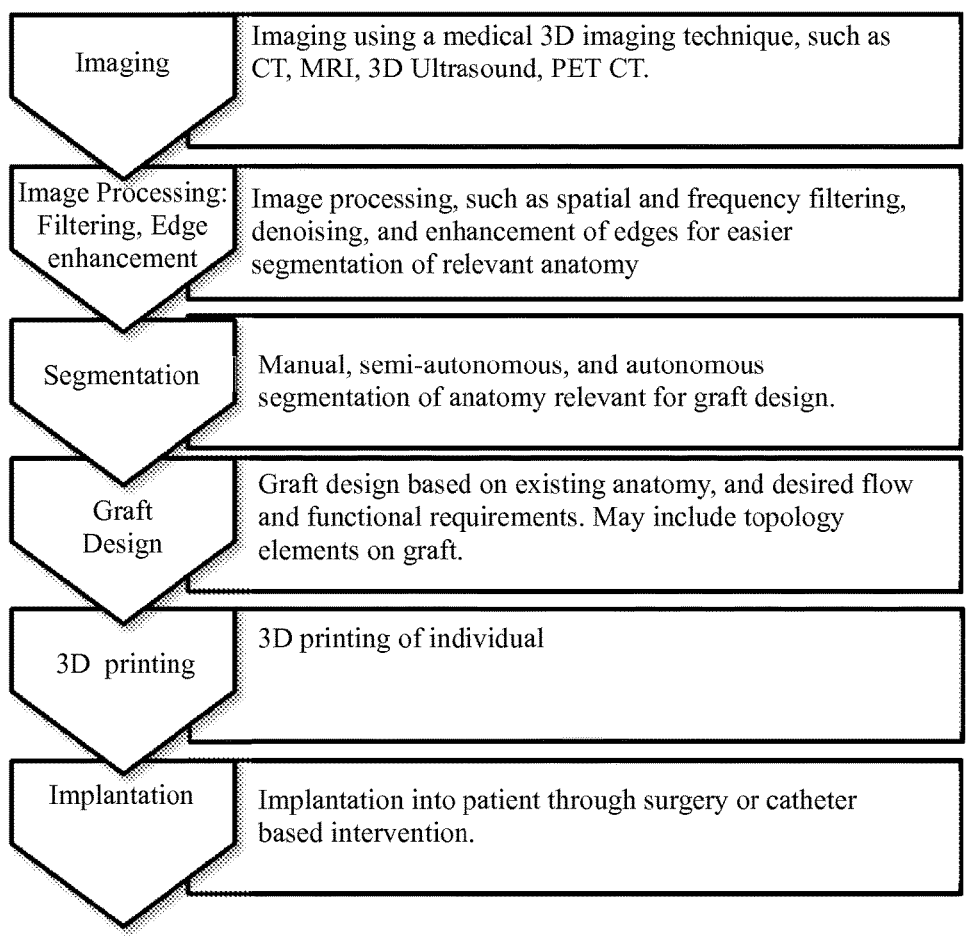
FIG. 4. Schematic representation of an embodiment where an image obtained from an individual is processes to design a blood vessel which can then be printed using 3-D printing of the materials of the present disclosure.
Figure 7:
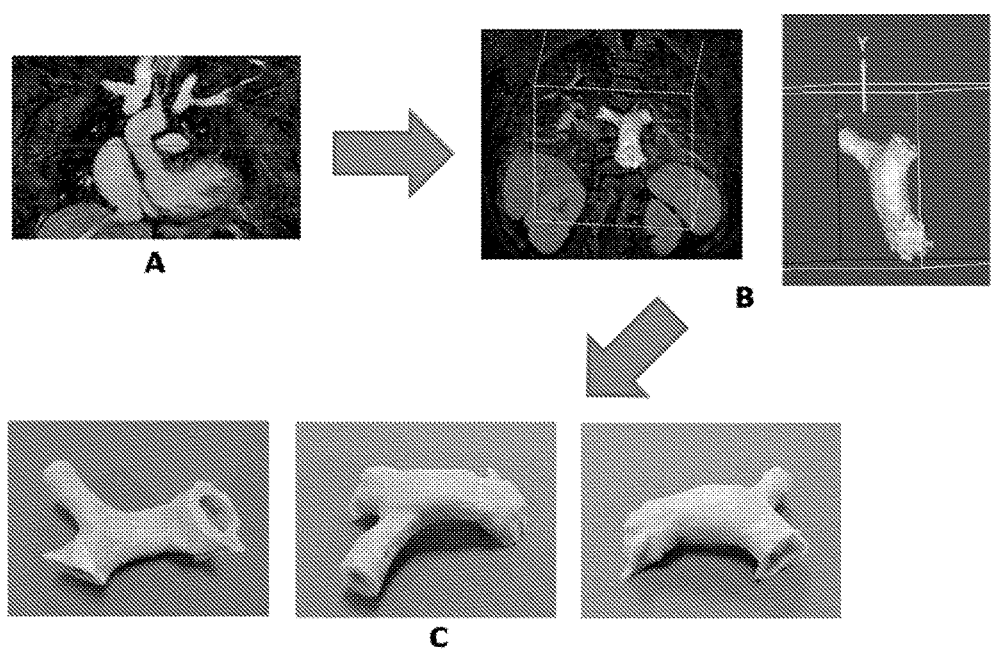
FIG. 7. Diagram showing an example of the process of segmentation of 3-D image data to print a patient specific model.

The biodegradable structure can be made using computer aided design (CAD) software. For example, FIG. 3 shows examples of CAD designed grafts. The biodegradable structure may be made based on the anatomical structure of an individual. For example, FIG. 4 shows a schematic representation of the use of an image from an individual to generate a design of a biodegradable structure (e.g., a blood vessel) and FIG. 7 shows an example of use of an image from an individual to generate a design of a biodegradable structure. In an embodiment, the method of making a biodegradable structure further comprising generating a design of the biodegradable structure based on images of an individual, wherein the selected portion of the composition is selected according to the generated design.

In an embodiment, a patient-specific biodegradable vascular graft that can promote and support neotissue growth can be can be designed and printed from the pre-operative 3-D images (CT, MRI, ultrasound, etc.) using 3-D printing technology. This "tailor-made" graft will be sized and shaped for surgery, which will expedite and standardize the corrective surgical procedure. Through this effort, the quality and safety of an operation can be improved and a new industrial field for pre-designing of vascular grafts will be created.

Figure 5:
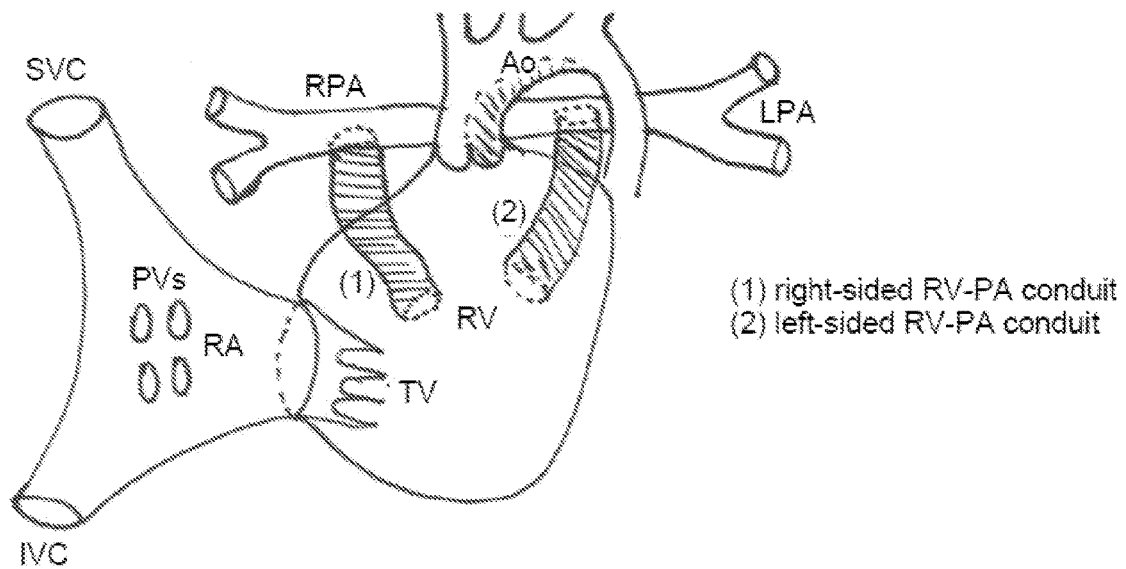
FIG. 5. Schematic representation of RV-PA Conduit in Hypoplastic Left Heart Syndrome.①  is right-sided RV-PA conduit.② is left-sided RV-PA conduit.
Figure 6:
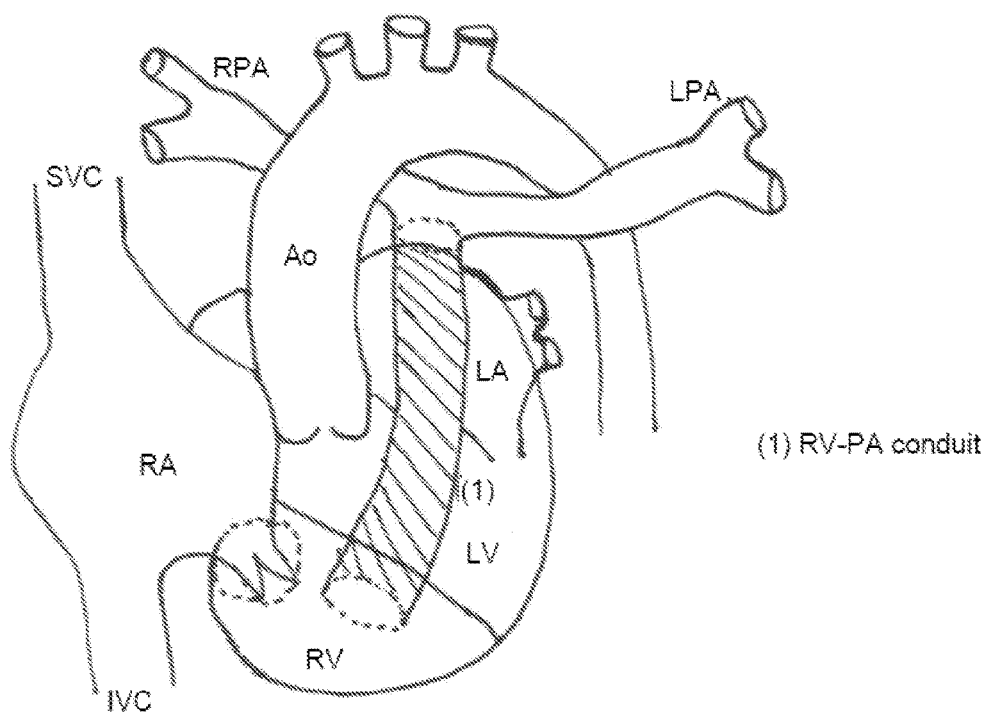
FIG. 6. Schematic representation of RV-PA Conduit in Setting of Right Ventricular Outflow Tract Obstruction.① is RV-PA conduit.

The products of the present disclosure have many applications. For many forms of congenital heart disease, surgical intervention involves the use of a right ventricle-to-pulmonary artery (RV-PA) conduit. FIGS. 5 and 6 show schematic representations of RV-PA conduit in Hypoplastic Left Heart Syndrome. Conditions which often require creation of a RV-PA conduit include tetralogy of Fallot, pulmonary stenosis and atresia, and hypoplastic left heart syndrome. Current surgical practice for creation of a RV-PA conduit involves the use of a standard synthetic tube graft that is shaped to the correct length and then anastomosed proximally to the right ventricle and distally to the pulmonary artery, therefore, bypassing the pulmonary valve and creating an alternative right ventricular outflow tract. As the shape and anatomy of patients with congenital heart disease are enormously varied, long-term surgical experience and expertise are required to properly design the conduit in the limited time frame available during surgery.

Anatomical data may be used to create a new biodegradable structure to replace an existing structure or a pathway between two structures, for example, vascular and cardiovascular structures. Replacement grafts can be designed and fabricated prior to surgery using imaging technologies such as ultrasound, computed tomography (CT), and magnetic resonance imaging (MRI) and 3-D patterning. For example, patient-specific tissue engineered vascular grafts (TEVGs) can play an important role (e.g., to accommodate patient growth/maturity and/or anatomical anomolies) in the treatment of cardiovascular disease by providing custom-tailored grafts with optimum flow profiles even for complex geometries, which can have a profound impact on the in vivo performance of the graft.

In an embodiment, a 3-D model of the graft is imported into a CAD software package (e.g., Autodesk Inventor Professional). For example, FIG. 11 shows the workflow used to generate the patient-specific RV-PA conduit. In this example, the stenosed conduit was digitally isolated and removed (equivalent to the surgical removal of the old conduit). A new conduit was designed to optimally fit the existing anatomy while avoiding compression of the coronary artery.

The CAD software can be used for computational fluid dynamics (CFD) analysis to evaluate hemodynamic parameters and optimize the graft design. For example, pre-operative pressure and flow values are used as boundary conditions.

For example, a stenosed conduit creates a large pressure differential that is relieved upon replacement of the RV-PA conduit. Thus, a CFD analysis was run using average hemodynamic parameters post RV-PA conduit implantation as boundary conditions. It is desirable that there is close to zero pressure drop across the conduit and no areas of turbulence or settling that might lead to clot formation. By determining the pressure drop across our conduit in the graft model, the design can be modified to minimize the pressure drop while maintaining the surgeon-recommended patient age-specific conduit diameter. FIG. 11 shows flow and pressure analysis for the patient-specific RV-PA conduit and for the old stenosed conduit, where the new conduit had a 0.15-0.9 mmHg pressure drop and the stenosed conduit had a 40 mmHg pressure drop.

Besides this example, TEVGs could be used in other applications such as the replacement of the aortic root or in the treatment of aortic aneurysms where surgeons must make custom modifications to traditional grafts prior to implantation. The material selection and processing can be used to tune the mechanical properties of the graft as well as the endothelialization of the graft, which in turn will impact the safety and long-term results of the surgery.

The use of the present disclosure to create a patient-specific tissue-engineered vascular graft allows for pre-operative creation of a vascular graft that is shaped to match each specific patient's anatomy in both structure and size. This graft requires minimal modification in the operating room, therefore, making the surgery easier and simpler. Furthermore, achieving the proper conduit shape as calculated from computer flow dynamics simulation would benefit the patient by preventing, for example, conduit stenosis and maintaining good cardiac function long term.

In order to create vascular grafts in a patient-specific manner, 3-D pre-operative imaging studies, including computed tomography imaging, magnetic resonance imaging, positron emission tomography-computed tomography imaging, and 3-D ultrasound imaging, is utilized. Imaging data from a specific patient is obtained and used to create 3-D computer models of the patient's anatomy. These models are segmented and refined to isolate the anatomical structures of interest in each individual patient. An appropriate vascular graft is then designed using CAD technology and flow dynamics calculations based on the patient's unique anatomy. The designed patient-specific vascular graft can then be fabricated, e.g., printed using a 3-D printer or using stereolithography or digital light processing.

Although useful in the creation of RV-PA conduits, patient-specific vascular grafts have diverse intrathoracic and extrathoracic vascular applications. Other uses of the patient-specific vascular grafts include, for example, applications in Fontan conduits/total cavopulmonary connection, modified Blalock-Taussig shunts, aortic arch reconstruction, interrupted aortic arch repair, coarctation of the aorta repair, truncus arteriosus repair, aortic aneurysm repair (ascending thoracic, descending thoracic, thoracoabdominal, abdominal), conduits with valves (including valved RV-PA conduits), patches with valves (as in Tetralogy of Fallot repair), patches for angioplasty, and valves and rings for valvuloplasty (aortic, mitral, tricuspid, pulmonary). Additionally patient specific conduits can be developed to assist with vascularization of transplant organs to better suit the anatomy of the patient.

An additional benefit of patient-specific vascular grafts is the use of biodegradable, biocompatible material to create the grafts. By utilizing biodegradable, biocompatible material, over time the implanted grafts will be degraded by the body resulting in a vascular graft that will ultimately become entirely composed of native tissue. This allows for growth of the created blood vessel as a child or other patient ages. As a result, further heart surgeries for conduit changes and upsizing can be avoided or minimized in the congenital heart surgery patient.

In addition to the patient specific fabrication of vascular conduits, the same patient-specific prosthetic design and printing methodology can be applied to valve annuloplasty rings. The most common defect leading to mitral dysfunction is the dilation of the valve annulus. In such cases, it may be necessary to repair the valve by adjusting the physiological dimensions of the valve opening. Ring-shaped devices may be implanted to correct annular dilation, reinforce annular suture lines, and correct increases in valve leaflet coaptation.

Like congenital defects, valve anatomy of patients demonstrating indications for valve repair with annuloplasty prostheses demonstrate varied geometrical attributes in valve anatomy. A significant drawback of current annuloplasty prostheses is that the rigid devices cannot be actively customized to best fit patient anatomy. Clinicians must choose devices based on preset sizes and shapes. Providing a technique to produce a custom-shaped device specific to the patient would allow the optimal size and shape of an annuloplasty ring for patients.

Methods of making the biodegradable structures may include additional steps such as, for example, isolation (e.g., drying) of the biodegradable structure, exposing the biodegradable structure to ultraviolet radiation such that additional crosslinking bonds are formed, and decontaminating/sterilizing the biodegradable structure. In an embodiment, the method of making the biodegradable structure further comprises one or more such step.

The steps of the method of making a biodegradable structure described in the various embodiments and examples disclosed herein are sufficient to carry out the method. Thus, in an embodiment, the method consists essentially of a combination of the steps of the methods disclosed herein. In another embodiment, the method consists of such steps.

In yet another aspect, the present disclosure provides biodegradable structures. In an embodiment, the biodegradable structure is a biodegradable implantable structure. The biodegradable structures (e.g., biodegradable implantable structure) may be tubular such as artificial blood vessels or cardiovascular scaffolds. In an embodiment, the biodegradable implantable structures (such as blood vessel or cardiovascular scaffold) is formed by a method of the present disclosure. In an embodiment, the biodegradable structure (e.g., a cardiovascular scaffold) is formed by a method of the present disclosure.

Depending on the choice of fabrication technique, cross-linking, and copolymer/polymer blend, PPF-based scaffolds may encompass structures such as, but not limited to, macroporous, hydrogel, emulsion, and/or solid scaffolds. For example, you can control porosity via molding or printing, but controlling precise porosity may not be easily attained with electrospinning.

The biodegradable structure may be surface functionalized. A variety of surface modifications be made to PPF structures to enhance in vivo functionality. Surface architecture can be controlled to create features, such as surface roughness and porosity, to enhance cellular attachment, infiltration, and proliferation. Surface architecture may be controlled via fabrication (mold casting or stereolithography) or modified after bulk scaffold fabrication. Examples of post-fabrication physical surface alterations may include porogen leaching, chemical vapor deposition, plasma etching, and UV irradiation. Inclusion of salts during fabrication and curing, such as sodium chloride, and subsequent salt leaching can be used to incorporate random pore architecture.

Chemical surface modification may also be utilized to enhance PPF-based scaffold surfaces based on the chemical structure of the polymer Immobilization of biomolecules such as peptide sequences and growth factors may be used. Biofunctional molecules may be included utilizing techniques including, but not limited to, passive coating, covalently linking, and peptide linking. Surface modifications may be utilized to elicit responses from cells and tissues, such as cell adhesion, proliferation, differentiation, paracrine and endocrine signaling, and morphological adaptation.

Biodegradable implantable structures according to the present disclosure include grafts such as grafts which are conduits, grafts with valves, grafts with various topography, grafts specific to patient anatomy, grafts that grow with the patient, grafts made from biodegradable, non-biodegradable, or combination materials, cardiac valves (aortic, mitral, tricuspid, pulmonary), cardiac valve rings (aortic, mitral, tricuspid, pulmonary), cardiac patches (angioplasty, intraventricular repair, ventricle), cardiac patches with valves, occluders or coils for shunts, grafts that are chemically modified post-printing, cardiac patches that are chemically modified post-printing.

In an embodiment, the cardiovascular scaffold comprises PPF or a copolymer comprising one or more PPF block(s) having a peptide, a protein, a growth factor, small signaling molecules, vitamins, drugs, a combination thereof, or a moiety comprising one or more thereof that is/are non-covalently or covalently attached to a surface of the cardiovascular scaffold.

In still another aspect, the present disclosure provides methods of using the biodegradable implantable structures including artificial blood vessels and cardiovascular scaffolds of the present disclosure. In an embodiment, a method for delivery of blood to or from an affected area in an individual (e.g., a human or non-human animal) that is not receiving adequate blood comprises the steps of: a) constructing an biodegradable structure (e.g. a biodegradable tubular structure) according to the method of the present disclosure or providing a biodegradable structure disclosed herein; and b) implanting the constructed structure in said individual such that blood flow through the implanted structure delivers blood to or from the affected area.

In other specific embodiment, the implantation of the biodegradable structures (such as cardiac valves and the like) can serve as replacement for the damaged or defective original structure and support the functioning of the cardiovascular system. It is expected that over time, the implanted structure will degrade while at the same time providing a scaffold for the growth of cells and thereby regeneration of the structure.

The steps of the method of using the biodegradable structures described in the various embodiments and examples disclosed herein are sufficient to carry out the method. Thus, in an embodiment, the method consists essentially of a combination of the steps of the methods disclosed herein. In another embodiment, the method consists of such steps.

In an embodiment, the biological structure is selected from blood vessels, valve leaflets, ventricles, atriums, septums, or any other cardiac or vascular structure (such as cardiac valves (aortic, mitral, tricuspid, pulmonary), cardiac valve rings (aortic, mitral, tricuspid, pulmonary), cardiac patches (angioplasty, intraventricular repair, ventricle), cardiac patches with valves, occluders or coils for shunts).

While the invention has been described through specific embodiments, those skilled in the art will recognize that routine modifications to the disclosure can be made and such modifications are intend to be within the scope of this disclosure.

EXAMPLE 1

This example describes identification of resin formulations according to the present disclosure.

Table 1 in FIG. 8 provides data on a variety of printing resin formulations investigated during our exploration of using PPF-based printing resins. The DEF:PPF ratio was adjusted mostly to adjust the viscosity of the printing formulation, but has also been found to have some effect on the mechanical properties of the printed part due to the inclusion of DEF monomers instead of purely PPF polymer chains. Overall, increasing amounts of DEF decrease the viscosity at room temperature and eases 3-D printing with the resin. However, too much DEF will prevent printing due to increased unavailability of longer PPF polymer chains that form the backbone of our printed constructs. PPF molecular weight refers to the molecular weight of the PPF used as the base of the polymer resin. Increased the molecular weight may increase the mechanical properties, such as stiffness and tensile strength, of the printed parts. Also, increased molecular weight may improve printing ability due to increased availability of carbon-carbon double bonds used to crosslink PPF polymer chains. BAPO induces photopolymerization Inhibitors (1 and 2) are used to prevent diffusive crosslinking, thus improving printing resolution. Too much inhibitor can prevent successful printing. Light brightness refers to the intensity of the light used in printing as adjusted on the EnvisionTEC Perfactory device used in these experiments. Exposure time for 50 micron layers refers to the length of time that each layer of the part is exposed to light before the exposing the next layer of the fabricated device to light. This, too, is controlled via the printer and not the resin, but demonstrates another factor used in the process of 3-D printing with the PPF resin. Results demonstrate the outcomes of these various components and printing conditions.

PPF is first synthesized by known methods and synthesis is ceased when the polymer reaches the desired molecular weight. Synthesis involves a two-step reaction of diethyl fumarate and propylene glycol in the presence of a $ZnCl_2$ catalyst and hydroquinone inhibitor. The first step of the reaction involves heating of these components in an inert atmosphere resulting in a bis(hydroxypropyl)fumarate intermediate and ethanol distillate byproduct. For the second step, the bis(hydroxypropyl)fumarate intermediate undergoes transesterification to produce PPF. This takes place as alcohol groups from one bis(hydroxypropyl)fumarate intermediate replace the alkoxy group of another bis(hydroxypropyl)fumarate). The reaction is allowed to proceed until the desired molecular weight of PPF is achieved. To create the resin, the mass of a sample of PPF is measured. The mass is recorded and the PPF is then heated in an oven between 60-80° C. to reduce the viscosity of the polymer. The necessary mass of DEF is then calculated based on the 0.8:1 DEF:PPF ratio desired in the final resin product. The total theoretical mass of the combined DEF and PPF is used to calculate the necessary amounts of photoinitiators and inhibitors to be included. Each photoinhibitor and photoinitiator is massed separately and then combined into one beaker. After these components are added together, the DEF is added to that beaker. The inhibitor/initiator/DEF mixture is then stirred via a stir rod or magnetic stir bar on a stir plate for approximately 30-60 minutes, or until the inhibitors/initiators have completely dissolved within the DEF. Following this step, the heated PPF (60-80° C.) is added to the beaker containing the inhibitor/initiator/DEF mixture. The entire resin mixture is then heated at 60-80° C. for 30-60 minutes, or until the PPF has completely dissolved into the inhibitor/initiator/DEF formulation. After dissolving is complete, the mixture is allowed to cool to room temperature under gentle mixing. Once at room temperature, the PPF resin is ready to be used in the 3-D printing or digital stereolithographic fabrication process.

The printed PPF constructs were modified as follows. Fabricated parts are first washed with phosphate-buffered saline (PBS) solution. Following washing, fabricated parts are immersed in 0.05 2-(N-morpholino)ethanesulfonic acid (MES) buffer solution for 15 minutes. Parts are then submerged in a solution of 1% w/v heparin, 0.5 M 1-ethyl-3-(3-dimethylaminopropyl)carbodiimide (EDC), and 0.5 M N-hydroxysuccinimide (NHS) or N-Hydroxysulfosuccinimide (Sulfo-NHS). Parts may be incubated anywhere from 1 hr to 15 hrs at room temperature and subsequently washed with distilled water. At this point, grafts are incubated with the protein of choice. Antibodies, such as anti-CD34 antibodies, may be covalently crosslinked to the part, whereas VEGF is non-covalently immobilized to the surface due to heparin-specific binding domains on the VEGF molecule. Incubation time and concentration varies depending on the molecule and the intended saturation of the molecule on the printed part's surface.

While average diameters of these vessels are exceedingly small, therapeutic devices that may be printed for implantation might serves vessels from that range in diameters of approximately 1 mm to 6 mm for coronary arteries to diameter of up to 4 cm for aortas. Cardiac structures may differ drastically based on the anatomy to be replaced. Vessel wall thicknesses may range from a scale of microns for smaller vessels like capillaries to 1.5-4 mm for the aorta. In contrast, bone applications are often intended for critical sized defects which are generally at least 1-2 cm in size depending on the particular bone. In a femur, a critically sized bone defect may be greater than 8 cm before it cannot heal on its own. This means that printed scaffolds must necessarily be much larger for bones and do not necessarily require the same precision as those for vascular structures.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A composition comprising:
    a) poly(propylene fumarate) (PPF) or copolymer comprising poly(propylene fumarate);
    b) a cross-linking monomer/co-monomer selected from fumarates;
    c) a photoinitiator selected from phosphine oxides;
    d) α-tocopherol; and
    e) hydroxyl-methoxybenzophenone,
    wherein the poly(propylene fumarate) (PPF) or copolymer comprising poly(propylene fumarate) is present at 50 to 100% by weight, the cross-linking monomer is present at 0.01 to 50% by weight, the photoinitiator is present at 0.5 to 3% by weight, the α-tocopherol is present at 0.01 to 0.3% by weight, and the hydroxyl-methoxybenzophenone is present at 0.01 to 30% by weight.

2. A method for making a biodegradable structure comprising the steps of:
    a) providing the composition of claim 1; and
    b) contacting the composition with visible radiation, ultraviolet radiation, or a combination thereof such that the biodegradable structure is formed.

3. The method of claim 2, wherein the contacting step comprises 3-D printing, stereolithography, or digital light processing.

4. The method of claim 2, wherein the biodegradable structure is selected from blood vessels, valve leaflets, ventricles, atriums, septums, cardiac valves, cardiac valve rings, cardiac patches, cardiac patches with valves, and occluders or coils for shunts.

5. A method for delivery of blood to or from an affected area in an individual that is not receiving adequate blood comprising the steps of:
    a) constructing an biodegradable structure according to claim 2, and
    b) implanting the constructed biodegradable structure in said individual such that blood flow through the implanted biodegradable structure delivers blood to or from the affected area.

6. The method of claim 5, wherein the biodegradable structure is selected from blood vessels, valve leaflets, ventricles, atriums, septums, cardiac valves, cardiac valve rings, cardiac patches, cardiac patches with valves, and occluders or coils for shunts.

* * * * *